United States Patent
Rosenberg

(10) Patent No.: US 10,489,379 B2
(45) Date of Patent: *Nov. 26, 2019

(54) COMPUTER-ASSISTED METHOD FOR ADAPTIVE, RISK-BASED MONITORING OF CLINICAL STUDIES

(71) Applicant: Alicia W Paladin, Chapel Hill, NC (US)

(72) Inventor: Michael Joseph Rosenberg, Port Orange, FL (US)

(*) Notice: Subject to any disclaimer, the term of this patent is extended or adjusted under 35 U.S.C. 154(b) by 535 days.

This patent is subject to a terminal disclaimer.

(21) Appl. No.: 15/205,179

(22) Filed: Jul. 8, 2016

(65) Prior Publication Data

US 2016/0328439 A1 Nov. 10, 2016

Related U.S. Application Data

(63) Continuation of application No. 14/604,586, filed on Jan. 23, 2015, now Pat. No. 9,418,098, which is a continuation of application No. 12/103,165, filed on Apr. 15, 2008, now abandoned.

(60) Provisional application No. 60/958,955, filed on Jul. 9, 2007, provisional application No. 60/926,577, filed on Apr. 27, 2007.

(51) Int. Cl.
| | |
|---|---|
| *G06F 16/23* | (2019.01) |
| *G06F 16/215* | (2019.01) |
| *G06F 16/245* | (2019.01) |
| *G06F 16/25* | (2019.01) |
| *G06F 16/2457* | (2019.01) |
| *G06F 19/00* | (2018.01) |

(52) U.S. Cl.
CPC ........ *G06F 16/2365* (2019.01); *G06F 16/215* (2019.01); *G06F 16/245* (2019.01); *G06F 16/24578* (2019.01); *G06F 16/252* (2019.01); *G06F 19/324* (2013.01)

(58) Field of Classification Search
None
See application file for complete search history.

(56) References Cited

U.S. PATENT DOCUMENTS

| | | | |
|---|---|---|---|
| 6,574,605 B1 * | 6/2003 | Sanders | G06Q 10/063112 705/7.26 |
| 7,496,661 B1 * | 2/2009 | Morford | H04L 41/5025 709/224 |

(Continued)

OTHER PUBLICATIONS

Ankur Jain et al, "Adaptive Stream Resource Management Using Kalman Filters", SIGMOD 2004, Jun. 13-18, 2004, Paris France, Copyright 2004 ACM 1-58113-859-8/04/06, 12 pages.*

*Primary Examiner* — Uyen T Le
(74) *Attorney, Agent, or Firm* — Ronald B. Goldstein

(57) ABSTRACT

A method and system are described for continuously assessing the quality of field data in a clinical study, identifying clinical sites with weaker performance than other sites, and flexibly allocating resources to address the problems, including the need to send field monitors to a site. The sites are compared with respect to the number of database entries requiring verification, and a higher priority (for allocation of management resources) is given to sites that have generated higher numbers of unverified database entries. The invention is particularly useful in the conduct of adaptive clinical trials of pharmaceutical products.

8 Claims, 4 Drawing Sheets

(56) References Cited

U.S. PATENT DOCUMENTS

2003/0037113 A1* 2/2003 Petrovykh ............... H04L 41/18
709/205
2006/0218285 A1* 9/2006 Talwar .................. G06F 9/5072
709/227
2007/0081468 A1* 4/2007 Timus ................... H04W 24/00
370/252

* cited by examiner

COMPUTER-ASSISTED METHOD FOR ADAPTIVE, RISK-BASED MONITORING OF CLINICAL STUDIES

CROSS-REFERENCE TO RELATED APPLICATIONS

This application is a continuation of U.S. Ser. No. 14/604,586, filed Jan. 23, 2015, now issued as U.S. Pat. No. 9,418,098, which is a continuation of U.S. Ser. No. 12/103,165, filed Apr. 15, 2008, and now abandoned. This application further claims priority from U.S. Provisional Application Ser. No. 60/926,577, filed Apr. 27, 2007, and from U.S. Provisional Application Ser. No. 60/958,955, filed Jul. 9, 2007, the disclosures of which hereby are incorporated by reference herein in their entireties.

BACKGROUND OF THE INVENTION

Field of the Invention

The invention relates to how data collected in field locations, often geographically diverse, is verified as being accurate. The comparison is made between data that have been collected, processed, and stored in a centralized location, along with any corrections or updates made since the data were first recorded, against original source data in the field. These steps are needed to verify the accuracy of data in the centralized database. Data refers to any information, including measurements, recordings, verbal responses, images (such as x-rays or CT scans), laboratory data, output from analyzers, or any other source, including electronic, paper, or other means.

Increasingly, clinical research is also under constraints to improve the ability to manage complex clinical trials, which are generally geographically diverse. Doing so requires continuous measurement of numerous performance indices, an easy reporting mechanism, and the ability to intervene or otherwise change processes, practices, or other elements to improve performance.

Description of the Related Art

Studies performed as part of evaluation of pharmaceutical products rely on different forms of data collected in the field, all of which must be accurately handled during collection, processing, and updating. It is therefore highly desirable, and may be required, that each piece of data that serves as the basis for analyzing the results of research, must accurately reflect field data. In pharmaceutical research, the first time a piece of data is recorded, it is considered "source," or the correct value. Any research, whether pharmaceutical or not, must have analyses based on data that are a true and accurate representation of such source data, and any group or individual conducting research must assure that data have been recorded and processed accurately and, when changes are made between the time data are first recorded and entered in the final database, that each step does not introduce errors. This is generally accomplished by comparing data in the final database against "source" data, which may be defined as the location in which a piece of data was first recorded.

Pharmaceutical research is generally conducted in hospitals, clinical, physician offices, and other medical locations in which source data may reside in patient's charts, which may be electronic or paper. Current systems of data entry fall into two general categories: most (about 50 to 60% of current clinical studies) involve recording a value on a paper Case Report Form ("CRF"), after which it is entered by a data entry clerk or the like, who types each value into an electronic system. A second verification entry ("double key entry") is then performed as a quality check. The other means of data entry, currently employed by approximately 40 to 50% of clinical trials, involves web-based Electronic Data Collection. This generally involves using a Worksheet onto which data are copied from source data (or "Source"), and from which the data then are keyed into an electronic system at the site.

In addition to the integrity of clinical data, data about the data themselves (meta-data) are useful and highly desirable means of measuring the practical aspects of how studies are conducted. These meta-data include site performance metrics such as error rates on data submitted, enrollment rates, and other elements key to the timely performance of each site and for the study overall. These data may be analyzed in different fashions, including point estimates, trends over time, or relative to other sites or performance measures and are described in U.S. Ser. No. 60/926,577.

Data are currently processed by comparing incoming data against as many as several hundred validation rules. These types of checks generally fall into three groups: (1) Range checks, which assure that a value for a data field falls within expected parameters and that the data are of the proper type (e.g., generally alpha or numeric); (2) Consistency, where an answer to one question may limit the responses to another question (for example, if subject is male, number of pregnancies should equal zero or Not Applicable); and (3) Trend information, where parameters may be specified for rate of change of certain variables (for example, a hemoglobin value may be consistent for the first four study visits but then drops precipitously, or height may be recorded as significantly lower than at previous visits). Being able to assess this information very quickly and to provide feedback to the sites that collected the data is very important to being able to assure that similar errors are not repeated.

Prior systems have utilized a web-based means of collecting data, transmitting this over computer networks or telephone lines, and putting data in a database. See, for example, U.S. Pat. No. 6,496,827, which discloses a system wherein data are input at a computer at the time of collection, for transmission over the internet to a central data storage site or database. The data are input in real time, via a graphical user interface that also provides means for rudimentary validation of the data. Further validation of the data occurs at the central site, via comparison with other data already in the database. However, systems such as those disclosed in U.S. Pat. No. 6,496,827 are limited by a lack of flexibility in how data are collected; require separate systems to perform data validation; and do not track study performance metrics.

The ability to analyze clinical data (and corresponding meta-data) is important and increasingly time sensitive, in part because the ability to produce more rapid decisions is based on the rapid availability of accurate data. This capability lies at the heart of adaptive clinical research, techniques and processes by which data and meta-data can be continuously reviewed and incorporated into changes in how studies are conducted. (In the context of the present invention, "adaptive" means that the course of such clinical investigations could be altered based on experience as a study progresses. Close monitoring of performance metrics allows early identification of weaknesses and allows these to be addressed, providing a more effective management system.) These changes may be, but are not limited to, study design, such as number or allocation of subjects, or to operational elements such as how to track performance of study sites or interviewers, subject recruitment strategies, and allocation of resources such as management.

Currently verification of site data is performed in one of two ways. The first is for data to remain at the site until a field monitor (also known as a "Clinical Research Associate" or "CRA") visits the site, at which time data are manually reviewed, errors that are detected are corrected on the scene, and data are then brought to a centralized location for data entry and computerized checking for range (allowable values), consistency (if one answer constrains answers that may appear elsewhere), and possibly other checks.

This method, however, has serious drawbacks in that such data and the corresponding meta-data typically are not available for weeks to months after they are actually generated, presenting serious obstacles to being able to measure elements such as site performance with sufficient time to allow effective management and seriously hampering, to the point of effectively precluding, the application of adaptive techniques to either strategic study elements or to the effective management of the study itself. This also creates considerably more work for clinical sites, since discrepancies are identified a long period of time after they are actually made, and the same mistakes may continue to occur in the interim. In addition, any errors that are identified require substantially more effort to go back and correct, since they occurred weeks ago, and paperwork already has been filed.

The second possibility is that data are submitted after they are generated, but before a monitoring visit has occurred. Under this scenario, data are entered and validation checks applied, usually at a centralized location. At some time after the data are received and validated (usually several weeks, but sometimes as long as several months), the monitor returns to the site to check each value in the centralized database against source data.

In either scenario, preparation for such a field visit occurs by printing out the database values, and printing a separate list of changes that occurred during the time between when a data point was first entered and the entry of its final value in the database. In practical terms, this often amounts to printing out several hundred sheets of paper, transporting these printouts to a clinic or other location where patients are seen, and comparing each value on the paper with a separate paper record of changes against the original ("source") data. This process is laborious, time-consuming, and error prone, since large stacks of paper are difficult to handle, sheets can be lost, and errors noted with follow-up flags (e.g., "Post-It Notes" or "stickies") can be lost because they are hidden from sight, fall off, or shift. Errors of omission can occur under such circumstances and often go undetected, since there is no backup mechanism whereby such errors would be suspected or detected. Each discrepancy that is noted results in an individually-written note (a "query") that must be transmitted to the site and also tracked as a change so that an "audit trail" is maintained. (An audit trail typically comprises a list of entries, each containing an old value, a new value, an identification of the person who changed the value, and the reason for the change.) The queries are generally returned to the site by fax. The entire process is time-consuming and similarly prone to error.

In either of these scenarios, a considerable amount of time is also required to prepare for a site visit and to enter the results of site work following the visit. In the first case, the field monitor has no guidance about where or what kind of errors might exist and may review several thousand fields during a typical monitoring visit. Remaining vigilant for errors during such a review is tedious and difficult, and field monitors with differing levels of experience may produce dramatically different results. Preparing for a field monitoring visit generally requires a day of preparation that includes printing out several hundred sheets of paper to prepare for a two-day site monitoring visit.

Thus, it would be desirable to be able to verify field data more promptly, and in a less labor-intensive and error-prone manner.

SUMMARY OF THE INVENTION

The above-identified shortcomings of the prior art are remedied by the present invention, which provides an electronic means of organizing, checking and comparing data, and writing and tracking discrepancies with respect thereto, as well as maintaining a corresponding audit trail. This system, coupled with the ability to transmit data and meta-data to a centralized site immediately after they are generated, greatly reduces the interval between when data are collected and when "clean" data are available for analysis and decision making. This facilitates both the strategic aspects of conducting adaptive trials (i.e., changing study design while in progress, such as number of patients, treatment assignment, or other aspects) as well as the tactical aspects (such as assessing and managing study progress through tracking performance indicators such as meta-data, an essential part of the adaptive process). In addition, the invention replaces much of the work presently done by hand with a uniform, standardized electronic process, improving its efficiency and enabling it to be utilized equally well when applied by highly experienced managers and field monitors as by those with considerably less experience. Finally, the invention's ability to perform these tasks by electronic means markedly improves the speed and accuracy of the process of checking source data and in identifying, recording, and resolving discrepancies that do occur.

As an example of time savings in preparing for a site visit, this tool allows a full copy of the database to be downloaded and prepared within minutes—a fraction of the time currently required.

Comparison of source with recorded data is easily achieved by the invention's ability to easily navigate all pages of a CRF. For any page, data recorded on that page can be called up, along with a record of any change made since the data were first entered (i.e., the audit trail). In a preferred embodiment of the invention, these data are provided with a status indicator, where fields that are unmonitored have a blank checkbox. After data in the database, as reflected by the computer screen, is compared with the source and determined to be correct, a check is placed in the box through clicking the computer mouse on the checkbox. In addition, individual fields with queries outstanding are marked in red, for example, since source verification cannot be performed on such fields where data are still being processed. Discrepancies between source and recorded data can be identified quickly and flagged for clarification in a query that is returned to the site for resolution. The inventive system thus provides a very quick and effective means of generating and tracking queries that are in a uniform format that facilitates query management across monitors and sites. This capability makes it far easier for site personnel, since every query they receive will be in a standardized format.

Thus, in a first embodiment of the invention, a method and a corresponding system are provided for performing source data verification as part of a clinical trial or other process that requires comparison of values in a database with source data at a plurality of geographically remote sites according to a set of procedures or parameters. The invention includes:
- (a) accessing a centralized database containing values representing the final product of source data that have been collected and/or recorded in the field;
- (b) comparing a value in the database with the corresponding source data;
- (c) determining whether the database value agrees with the corresponding source data; and
- (d) determining whether any queries have been generated with respect to such value during the period since the source data were originally collected, in which case the type and frequency of errors can help the monitor take steps to ensure that such errors are not repeated (through instruction, training, comparison with other sites, or other measures) or to determine why errors persist after one or more queries have been issued and addressed by the site.

In an additional embodiment of the invention, step (d) further includes displaying the audit trail of any changes made to such value since the time it was first recorded.

In a further embodiment, the invention includes: (e) if it is determined according to step (c) that the database value does not agree with the source data, generating a new query with respect to such data.

In another embodiment, the invention includes: (f) if it is determined according to step (c) that the database value agrees with the source data, creating a record that such value has been verified.

In yet a further embodiment, the invention includes:
- (g) electronically reporting the audit trail of step (d) or the new query generated in step (e), along with the data corresponding to such audit trail or new query, to an entity capable of determining whether the data require correction or whether procedures or parameters utilized in conducting said clinical trial or other process require modification; and
- (h) providing instructions, based on the reported data, to
  - (1) correct the data, or
  - (2) follow or modify the procedures or parameters utilized in conducting said clinical trial or other process.

BRIEF DESCRIPTION OF THE DRAWINGS

FIG. 2 depicts a Microsoft Windows® dialog box, customized according to the invention, to perform site monitoring.

FIG. 3 depicts a secondary Windows® dialog box that may be used, as a preformatted Query Template in accordance with the invention, to create a query with respect to a discrepancy in a particular data field shown in FIG. 2.

FIG. 4 depicts an example of an audit trail, as may be displayed through the dialog box shown in FIG. 2 or FIG. 3.

DETAILED DESCRIPTION OF THE INVENTION

Figure 1:
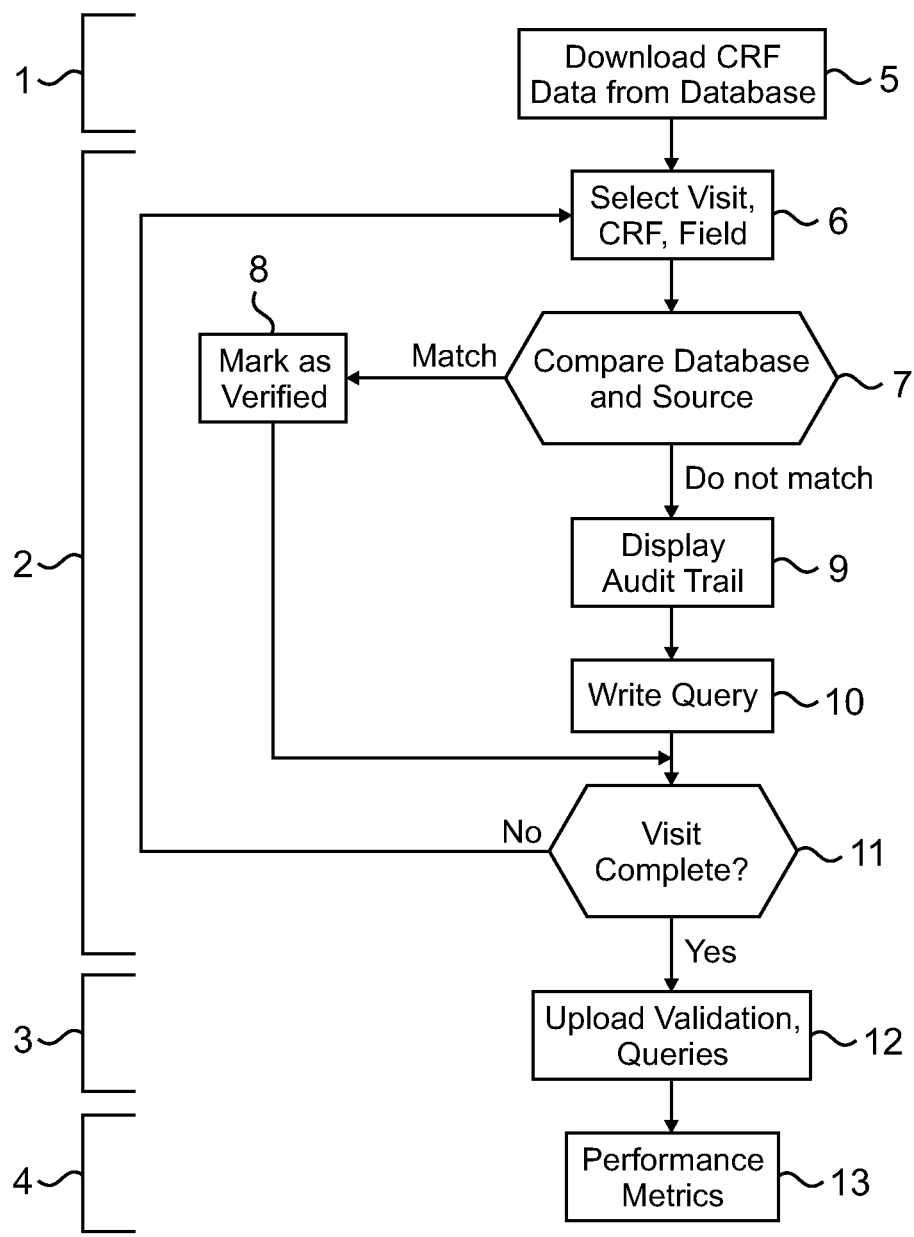
FIG. 1 is a flow chart depicting the operation of the source data checking process, depicting a preferred embodiment of a clinical trials system according to the invention.

Clinical trials are generally highly complex processes that involve collection of many thousands of data elements from multiple clinical sites, laboratory facilities, regulatory agencies, and often outside vendors such as companies supplying test drugs. Many of the foregoing may be in different countries, which present the challenges of different cultures, languages, time zones, and other differences that complicate the ability to effectively manage such diverse participants in a clinical evaluation. The quality of the data collected in such circumstances is of paramount importance, because accurate data are necessary to demonstrate the efficacy and safety of any pharmaceutical product being evaluated. Failure to optimize data quality slows study progress; requires a greater number of patients in order to demonstrate an effect; impairs the ability of a manager to change a study based on what already has occurred in the course of the study; and slows regulatory filings because of additional time required to assure "clean" data.

A preferred embodiment of a computerized system for source data verification according to the invention is shown in FIG. 1, wherein certain functions 1 are performed at a central location, before a monitor leaves to visit a participating site. Other activities 2 are performed while the monitor is at the specific site, and additional activities 3 can be performed at any site with access, through the internet or other means, to the central database; these typically include the clinical site, a hotel or other access point while traveling, or after the monitor returns to his/her office at the central location. The measurement of performance metrics also then may be accomplished 4 at a centralized location from which study activities are coordinated.

The process by which the invention is utilized is also shown in FIG. 1 and begins with downloading 5 the portion of data in the central database that pertains to the site(s) to be visited. This downloading typically occurs while the monitor is at the central location. A separate capability of the invention allows the number of unmonitored data fields to be continually reviewed with respect to each distinct site, so that management staff can determine when a site visit is justified. This also assists with predicting and scheduling resources such as field monitors and allows an adaptive approach to monitoring in that stronger or more experienced personnel can be sent out when a greater amount of data have accumulated that need to be source verified, while less capable monitors might visit when smaller amounts of data have accumulated.

Figure 2:
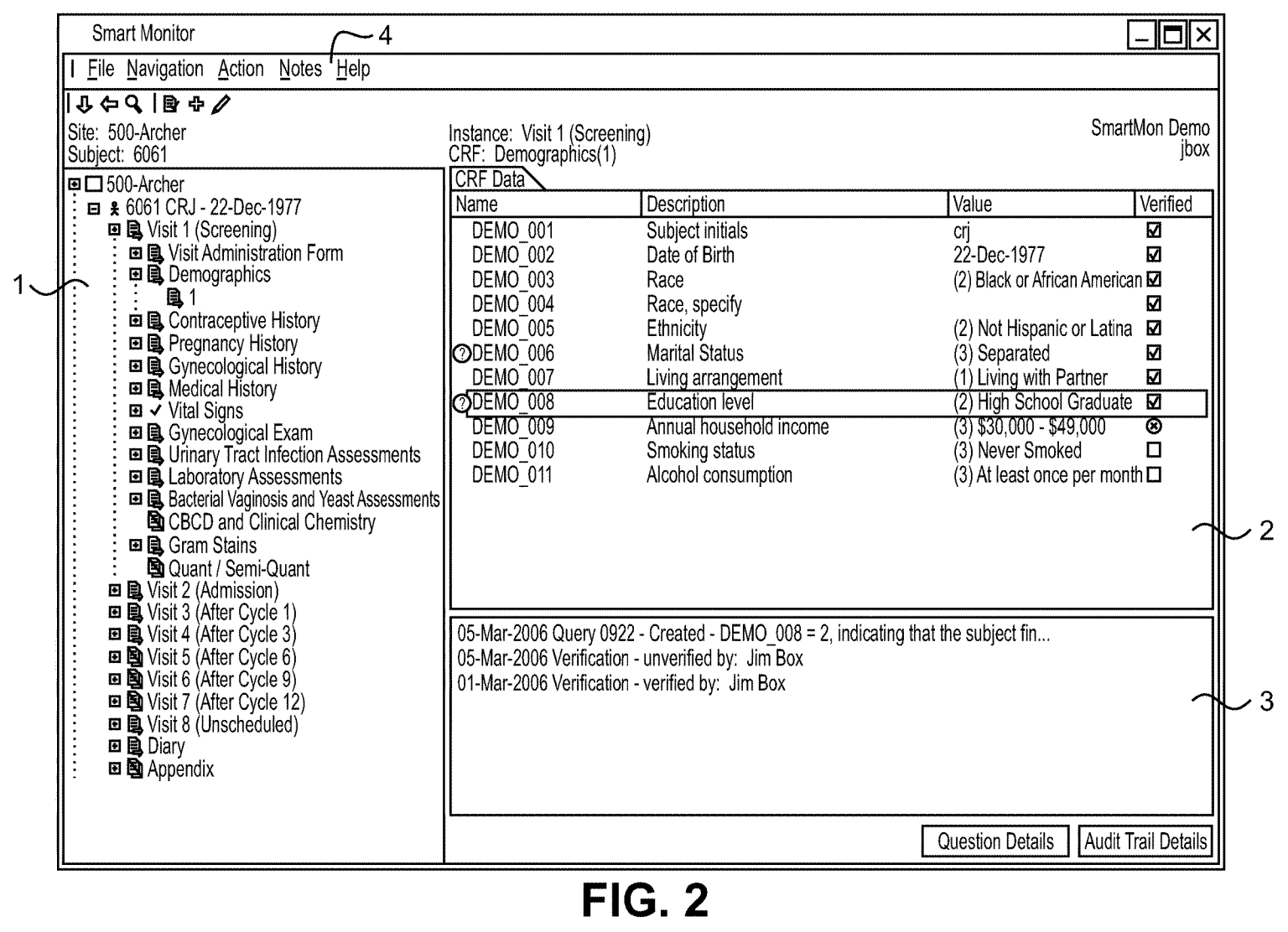

At the site, the monitor begins by opening a tree view of data that exist from the particular site. This lists each patient in the study, each visit, and each CRF (or "form") completed at each of the visits. The monitor selects 6 a visit and a form, and may select a particular data field in the form. In a preferred embodiment of the invention shown in FIG. 2, the invention shows the variable name, description, value in the database, and verification status for each data field in the form. In FIG. 2, the tree view showing each patient, visit, and form is displayed in the left pane 1 of the Windows® dialog box. After a particular visit is selected, each variable on the form selected is displayed, along with the variable name, description, value, and verification status in the upper right pane 2. If any changes have been made to the data since the time they were submitted, each change is chronologically noted in the lower right pane 3, facilitating tracking of changes. Lower right pane 3 also provides separate "buttons" that can call up the full text of a specific CRF question ("Question Details") or the details of an existing or previous query ("Audit Trail Details"). A menu 4 at the top of the dialog box provides tools for navigation among a site's patients in the study, and among the various visits and forms for each patient, and also provides access to Query Templates, Notes, Help, and other tools and aids.

The invention also displays when an active query exists with respect to a particular field, in which case source verification cannot be performed until the active query is resolved. (In the preferred embodiment shown in FIG. 2, outstanding queries are indicated by a Question Mark symbol immediately to the left of the variable name in upper right pane 2 of the dialog box.)

Referring now back to FIG. 1, each value in the database then is physically compared 7 with the Source (accounting for any changes that may have occurred since submission), to determine whether the data are in agreement. If the Source agrees with the CRF value, the monitor marks the data as verified 8. As shown in FIG. 2, the verification status ("Verified") field in pane 2 has a box that is unchecked if verification has not been completed, and is checked if the data are in agreement. Moreover, if certain fields are not available for verification (for example, if a query is outstanding, as described above), this also is indicated in the "Verified" field, for example, by a red circle with an X through the middle. (When those queries are resolved and the corresponding data are eligible to be source verified, the status change is indicated by the appearance of an unchecked box in the "Verified" field.)

Figure 4:
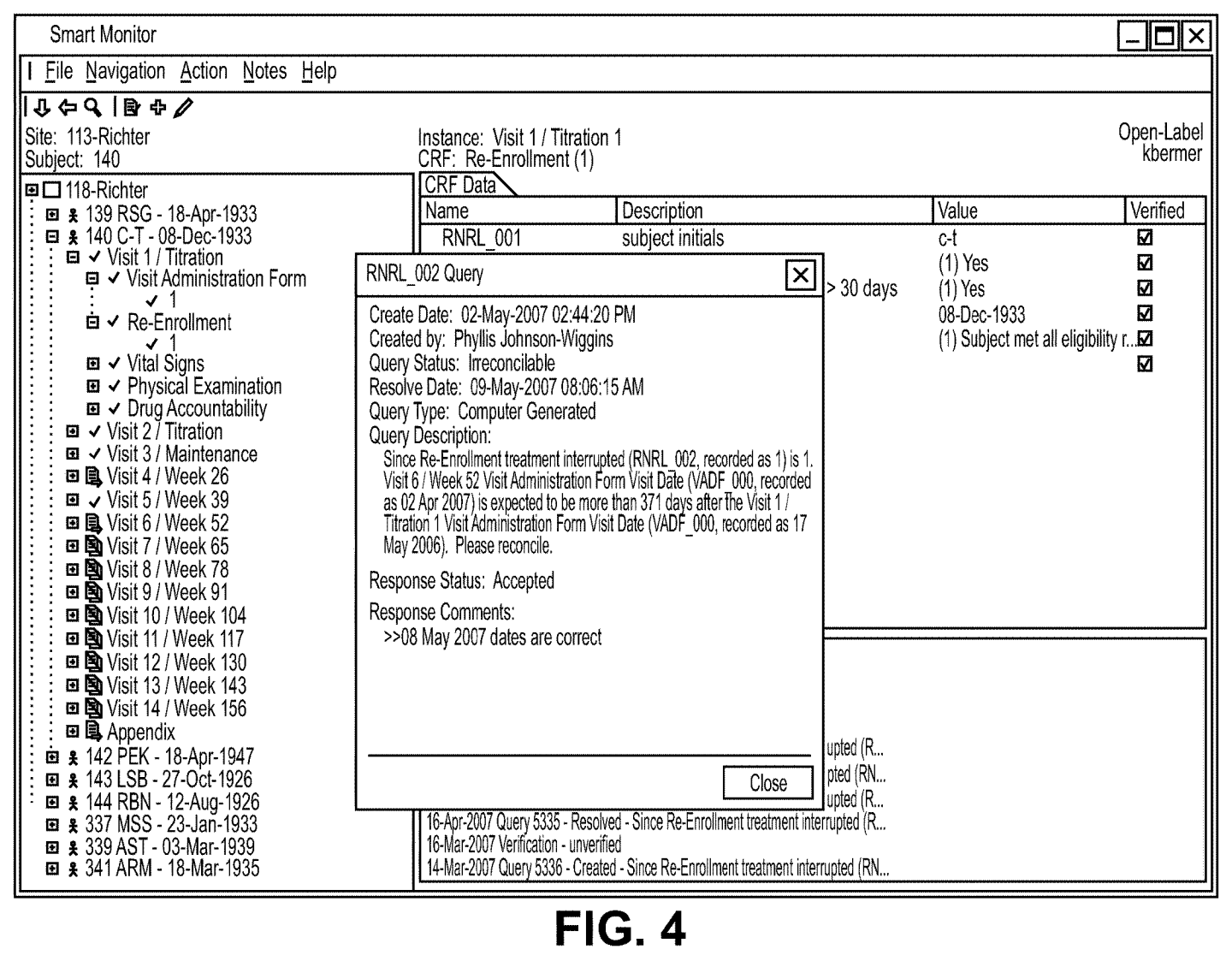

Continuing in FIG. 1, if queries have been generated since the data were originally submitted, each query is listed in chronological order (i.e., the Audit Trail is displayed) 9 so that the monitor can track each change. A representative example of such a list appears in FIG. 2, in lower right pane 3. In this instance, it can be seen that three queries have been issued regarding the highlighted data field in pane 2. Clicking on each of these reveals details, including the individual who initiated the query, the date, and the nature of the question, as shown in FIG. 4.

Figure 3:
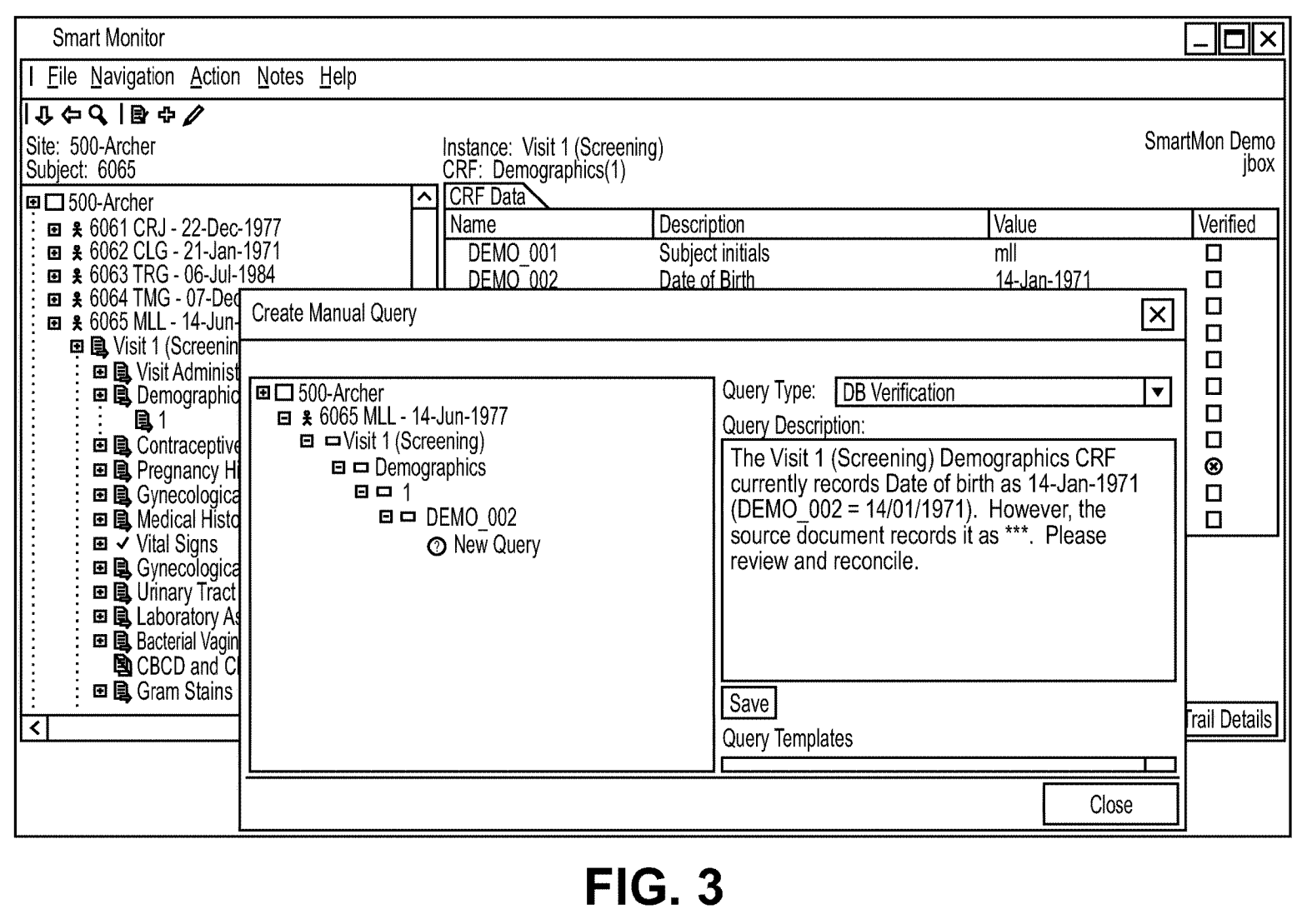

Regardless whether queries previously have been generated with respect to a particular data field, if there currently is disagreement between the Source and the CRF value in such data field, a query now must be generated. In this case, the monitor selects the discrepant field (as shown, for example, in FIG. 2), selects a button to create a query and, in a new dialog box that opens as a preformatted Query Template (see, for example, FIG. 3), enters the value from the source document. Thus, as shown in FIG. 1, a query summarizing the discrepant results thus is automatically generated 10 using preformatted Query Templates, modifying each as necessary for the circumstances.

The process in FIG. 1 continues with a determination 11 of whether the visit is completed. If the visit has not been completed, the monitor selects 6 another visit and form (or another data field in the form previously selected), and repeats the process described in the foregoing paragraphs. It should be noted that the present invention also has the ability, at any point in the process, to call up electronic notes that may be appended to any field.

If the visit has been completed, updated data (which may include new queries, status of verification, notes) are normally uploaded 12 to the centralized database. However, the user can connect to the centralized database at any time, including during the course of the site visit, e.g., at a hotel, through a telephone connection or any other means by which data can be transferred.

The invention further provides the additional, essential capability of intervening in response to issues that can be improved. Knowledge of a problem or issue (based on certain data collected and verified as set forth in the preceding paragraphs) sounds an alarm to intervention, which can be implemented through any conventional manner appropriate to the circumstance and problem. For example, if it becomes apparent that a single question on a CRF produces an inordinate number of queries or poor quality data, the wording of such question can be re-evaluated. If the clarity of the question can be improved, such question can be re-worded as appropriate. As another example, if the data somehow indicate that an individual site is having problems, the invention enables a site monitor or project manager to "drill down" in order to better understand the source of such problems. Thus, the site monitor or project manager may detect from the data that one particular interviewer has a higher query rate than others at such site or elsewhere within the study. In that case, it is possible for the manager to intervene to determine whether the problem is one of inadequate training, time, or other factors with respect to such interviewer.

Thus, continuing in FIG. 1, following upload 12 of the primary data, performance metrics may be created and/or updated 13, based on the primary data, to reflect most recent experience. The immediacy of such data is key to the notion of modifying trials in progress, either by strategic measures (which critically depend on very quick availability of accurate data) or tactical measures, such as query rates, response times, screening and enrollment measures. The latter are particularly important to being able to modify suboptimal performance, and similarly depend on timely measurement and availability of such metrics.

In a preferred embodiment, the invention enables a "Site Performance Index" as an overall measure of the respective sites' abilities to measure quality of data. This Index may include various measures such as query rate, time to respond to queries, and other measures that can together form a simple, convenient measure of how well the various sites perform, and thus guide oversight efforts. For each site, this information is compared against average values for all sites, and each field monitor can continuously track this as a key performance indicator.

The foregoing description details certain embodiments of the invention. It will be appreciated, however, that the invention can be practiced in many ways. It also should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A risk-based, computer-assisted method for adaptively adjusting the allocation of management resources in a medical clinical trial conducted at a plurality of remote sites, said method comprising the steps of:
    (a) accessing a centralized database containing values representing the current product of data previously collected and/or recorded at said remote sites;
    (b) ascertaining, with respect to each remote site, the number of values in said database that are to be verified for accuracy;
    (c) comparing the number of values ascertained in step (b) for the respective remote sites, so as to rank the respective sites according to said numbers;
    (d) determining the priority of each remote site with respect to verifying the accuracy of values in said database, based on the comparing in step (c), wherein said priority is greater for a site for which a higher number was ascertained in step (b) than for a site for which a lower number was ascertained in step (b); and
    (e) adjusting the allocation of management resources to one or more sites, according to the priority determined in step (d).

2. The method of claim 1, wherein said management resources comprise field monitoring.

3. The method of claim 2, wherein the allocation of field monitoring is increased for one or more sites having a higher priority as determined in step (d).

4. The method of claim 2, wherein the allocation of field monitoring is decreased for one or more sites having a lower priority as determined in step (d).

5. A computerized system for adaptively adjusting the allocation of management resources in a medical clinical trial conducted at a plurality of remote sites, said system comprising:
(a) a centralized database containing values representing the current product of data previously collected and/or recorded in the field;
(b) means for ascertaining, with respect to each remote site, the number of values in said database that are to be verified for accuracy;
(c) means for comparing the number of values ascertained in paragraph (b) for the respective remote sites, so as to rank the respective sites according to said numbers;
(d) means for determining the priority of each remote site with respect to verifying the accuracy of values in said database, based on the comparing in paragraph (c), wherein said priority is greater for a site for which a higher number was ascertained in paragraph (b) than for a site for which a lower number was ascertained in paragraph (b); and
(e) means for adjusting the allocation of management resources to one or more sites, according to the priority determined in paragraph (d).

6. The system of claim 5, wherein said management resources comprise field monitoring.

7. The system of claim 6, wherein the allocation of field monitoring is increased for one or more sites having a higher priority as determined in paragraph (d).

8. The system of claim 6, wherein the allocation of field monitoring is decreased for one or more sites having a lower priority as determined in paragraph (d).

\* \* \* \* \*